United States Patent
Reyes et al.

(10) Patent No.: US 11,554,260 B2
(45) Date of Patent: Jan. 17, 2023

(54) MULTI-INPUT SPEED RESPONSE ALGORITHM FOR A BLOOD PUMP

(71) Applicant: HeartWare, Inc., Miami Lakes, FL (US)

(72) Inventors: Carlos Reyes, Davie, FL (US); Katherine Chorpenning, Miami Lakes, FL (US); Antonio Luiz Silva Ferreira, Davie, FL (US); Neethu Lekshmi Vasudevan Jalaja, Miami, FL (US); Justin Wolman, Aventura, FL (US); Fernando Casas, Miami Lakes, FL (US)

(73) Assignee: HeartWare, Inc., Miami Lakes, FL (US)

( * ) Notice: Subject to any disclaimer, the term of this patent is extended or adjusted under 35 U.S.C. 154(b) by 315 days.

(21) Appl. No.: 16/359,501

(22) Filed: Mar. 20, 2019

(65) Prior Publication Data
US 2019/0307938 A1 Oct. 10, 2019

Related U.S. Application Data

(60) Provisional application No. 62/653,958, filed on Apr. 6, 2018.

(51) Int. Cl.
*A61M 60/148* (2021.01)
*A61M 60/422* (2021.01)
(Continued)

(52) U.S. Cl.
CPC ........ *A61M 60/538* (2021.01); *A61M 60/148* (2021.01); *A61M 60/178* (2021.01);
(Continued)

(58) Field of Classification Search
CPC .... A61M 1/101; A61M 1/1086; A61M 1/122; A61M 1/125; A61M 1/127;
(Continued)

(56) References Cited

U.S. PATENT DOCUMENTS 6,066,086 A * 5/2000 Antaki ................ A61M 60/50
600/17
6,139,487 A * 10/2000 Siess ........................ H02K 5/08
415/900
(Continued)

FOREIGN PATENT DOCUMENTS

WO 2017120451 A2 7/2017
WO WO-2017120451 A2 * 7/2017 .......... A61M 1/1031

OTHER PUBLICATIONS

International Search Report and Written Opinion dated Jun. 12, 2019 for International Application No. PCT/US2019/023181, International filing date Mar. 20, 2019; consisting of 12 pages.
(Continued)

*Primary Examiner* — Michael W Kahelin
*Assistant Examiner* — Pamela M. Bays
(74) *Attorney, Agent, or Firm* — Shumaker & Sieffert, P.A.

(57) ABSTRACT

A method of responding to an adverse event associated with an implantable blood pump including detecting the adverse event, reducing a pump speed of the blood pump relative to a set pump speed in response to the detected adverse event, and determining whether at least one of a group consisting of the adverse event and a second adverse event is present following the reducing of the pump speed of the blood pump. If the at least one of the group consisting of the adverse event and a second adverse event is not present, the method includes increasing the pump speed to the set pump speed and if the at least one of the group consisting of the adverse event and a second adverse event is present while (Continued)

increasing the pump speed to the set pump speed, the method includes reducing the pump speed to a maximum safe operating speed.

20 Claims, 9 Drawing Sheets

(51) Int. Cl.
 A61M 60/178 (2021.01)
 A61M 60/538 (2021.01)
 A61M 60/216 (2021.01)
 A61M 60/50 (2021.01)
 A61M 60/205 (2021.01)
(52) U.S. Cl.
 CPC ........ *A61M 60/216* (2021.01); *A61M 60/422* (2021.01); *A61M 60/205* (2021.01); *A61M 60/50* (2021.01)
(58) Field of Classification Search
 CPC ........ A61M 2205/3334; A61M 60/148; A61M 60/205; A61M 60/422; A61M 60/50; A61M 60/178; A61M 60/216; A61M 60/538
 See application file for complete search history.

(56) References Cited

U.S. PATENT DOCUMENTS

| | | |
|---|---|---|
| 7,997,854 B2 | 8/2011 | LaRose et al. |
| 8,007,254 B2 | 8/2011 | LaRose et al. |
| 8,419,609 B2 | 4/2013 | Shambaugh, Jr. et al. |
| 8,512,013 B2 | 8/2013 | LaRose et al. |
| 9,427,508 B2 | 8/2016 | Reyes et al. |
| 9,492,601 B2 | 11/2016 | Casas et al. |
| 9,511,179 B2 | 12/2016 | Casas et al. |
| 9,561,313 B2 | 2/2017 | Taskin |
| 2003/0199727 A1* | 10/2003 | Burke .................. A61M 60/50 600/16 |
| 2004/0215050 A1 | 10/2004 | Morello |
| 2014/0100413 A1* | 4/2014 | Casas .................. A61M 1/1015 600/16 |
| 2015/0367048 A1 | 12/2015 | Brown et al. |
| 2018/0085507 A1 | 3/2018 | Casas et al. |

OTHER PUBLICATIONS

International Preliminary Report on Patentability from International Application No. PCT/US2019/023181, dated Oct. 6, 2020, 7 pp.
Response to Communication Pursuant to Rules 161(1) and 162 EPC dated Nov. 13, 2020, from counterpart European Application No. 19715647.4, filed May 4, 2021, 27 pp.

* cited by examiner

MULTI-INPUT SPEED RESPONSE ALGORITHM FOR A BLOOD PUMP

CROSS-REFERENCE TO RELATED APPLICATION

This application claims the benefit of U.S. Application Ser. No. 62/653,958, filed Apr. 6, 2018, entitled MULTI-INPUT SPEED RESPONSE ALGORITHM FOR A BLOOD PUMP.

FIELD

The present technology is generally related to a method and system for detecting an adverse event associated with an implantable blood pump and performing an integrated response strategy in response thereto.

BACKGROUND

Implantable blood pumps are commonly used to assist the pumping action of a failing heart. Typically, blood pumps include a housing with an inlet, an outlet, and a rotor mounted therein. The inlet may be connected to a chamber of the patient's heart, typically the left ventricle, using an inflow cannula. The outlet may be connected to an artery, such as the aorta. Rotation of the rotor drives blood from the inlet towards the outlet and thus assists blood flow from the chamber of the heart into the artery. One known type of blood pump is a ventricular assist device ("VAD"). Exemplary VADs include the HVAD® pump and the MVAD® pump manufactured by HeartWare, Inc. in Miami Lakes, Fla., USA.

To provide clinically useful assistance to the heart, blood pumps impel blood at a relatively substantial rate. However, blood pumps may be associated with one or more adverse events, such as suction, occlusion, or high differential pump pressure. Suction is an intermittent decrease in flow through the pump, otherwise known as a mismatch between the pump output and venous return. Suction typically occurs at the pump's inlet due to volumetric depletion within a heart chamber or due to a proximity between the pump's inlet and a myocardial structure. Occlusion is a sustained decrease in flow through the pump which may occur at the pump's inlet when the pump's inflow is sealed due to a proximity between the pump's inlet and a myocardial structure. Methods exist which include decreasing the pump speed relative to a starting pump speed in attempt to resolve the frequency, duration, or severity of the adverse event. For example, at least one known method includes implementing separate speed response strategies in response to a suction condition and a high pump pressure, respectively, rather than providing a cohesive response strategy.

SUMMARY

The techniques of this disclosure generally relate to a method and system for detecting an adverse event associated with an implantable blood pump and performing an integrated response strategy in response thereto.

In one aspect of this disclosure, a method of responding to an adverse event associated with an implantable blood pump includes detecting the adverse event. In response to the detected adverse event, a pump speed of the blood pump is reduced relative to a set pump speed. Whether at least one of a group consisting of the adverse event and a second adverse event is present is determining following the reduction of the pump speed of the blood pump. If the at least one of the group consisting of the adverse event and a second adverse event is not present, the pump speed is increased to the set pump speed. If the at least one of the group consisting of the adverse event and a second adverse event is present while increasing the pump speed to the set pump speed, the pump speed is reduced to a maximum safe operating speed.

In another aspect, the method further includes detecting a clearance of the adverse event and gradually increasing the pump speed to the set pump speed in response thereto.

In another aspect, the method further includes maintaining the maximum safe operating speed during an optimization attempt.

In another aspect, the method further includes detecting the at least one of the group consisting of the adverse event and the second adverse event following the optimization attempt and repeating the reduction of the pump speed of the blood pump.

In another aspect, the method further includes detecting the at least one of the group consisting of the adverse event and the second adverse event during the optimization attempt and repeating the reduction of the pump speed of the blood pump.

In another aspect, the method further includes reducing the pump speed of the blood pump relative to the set pump speed in a plurality of rapid step-wise decreases when the adverse event is a suction event, determining a clearance of the adverse event following each of the plurality of rapid step-wise decreases, and discontinuing the plurality of rapid step-wise decreases when the clearance of the adverse event is detected.

In another aspect, the method further includes reducing the pump speed relative to the set pump speed in a single speed decrease when the adverse event is a high-pressure event.

In another aspect, the method further includes simultaneously detecting the adverse event and the second adverse event and reducing the pump speed of the blood pump relative to the set pump speed using one of a group consisting of the plurality of rapid step-wise decreases and the single speed decrease.

In another aspect, the method further includes generating a first alarm when the pump speed reaches a predetermined low speed threshold and the adverse events is not cleared.

In another aspect, the method further includes generating a second alarm when the pump speed is below a predetermined optimization range after a predefined number of attempts to optimize to the set pump speed.

In another aspect, the method further includes detecting the adverse event using a suction detection method, wherein the suction detection method is based on a difference between an average and a minimum of a back electromotive force signal multiplied by a difference between a maximum and the minimum of a back electromotive force signal.

In one aspect, a method of controlling an implantable blood pump includes detecting at least one an adverse event associated with the blood pump, the adverse event being one of a group consisting of a suction event and a high-pressure event a pump speed of the blood pump is reduced relative to a set pump speed in accordance with the at least one adverse event. Whether the at least one adverse event is present after reducing the pump speed is determined. If the at least one adverse event is not present, the pump speed is increased to the set pump speed. If the at least one adverse event is present during the pump speed increase, the pump speed is reduced to a maximum safe operating speed.

In another aspect, the method further includes maintaining the pump speed at the maximum safe operating speed during an optimization attempt in accordance with the determined presence of the at least one adverse event.

In another aspect, the method further includes generating a first alarm when the pump speed reaches a predetermined low speed threshold and the adverse events is not cleared.

In another aspect, the method further includes generating a second alarm when the pump speed is below a predetermined optimization range after a predefined number of attempts to optimize the set pump speed.

In another aspect, the method further includes detecting the adverse event using a suction detection method, wherein the suction detection method is based on a difference between an average and a minimum of a back electromotive force signal divided by a difference between a maximum and the minimum of a back electromotive force signal.

In another aspect, the method further includes reducing the pump speed of the blood pump relative to the set pump speed in a plurality of rapid step-wise decreases if identifying the adverse event as the suction event and reducing the pump speed relative to the set pump speed in a single speed decrease if identifying the adverse event as the high-pressure event.

In another aspect, the method further includes selectively reducing the pump speed using a lower speed value among at least one of a group consisting of the plurality of rapid step-wise decreases and the single speed decrease.

In another aspect, the suction event includes one of a group consisting of a suction event and an occlusion condition.

In one aspect, a system for responding to an adverse event associated with an implantable blood pump includes a processor and a control circuit in communication with the processor and the blood pump, the control circuit being configured to detect the adverse event, execute a speed reduction response including reducing a pump speed of the blood pump relative to a set pump speed in response to the adverse event, detect a presence of at least one of a group consisting of the adverse event and a second adverse event following the speed reduction response, and if the at least one of the group consisting of the adverse event and the second adverse event is not present, increase the pump speed to the set pump speed, and if the at least one of the group consisting of the adverse event and the second adverse event is present while increasing the pump speed to the set pump speed, reduce the pump speed to a maximum safe operating speed.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
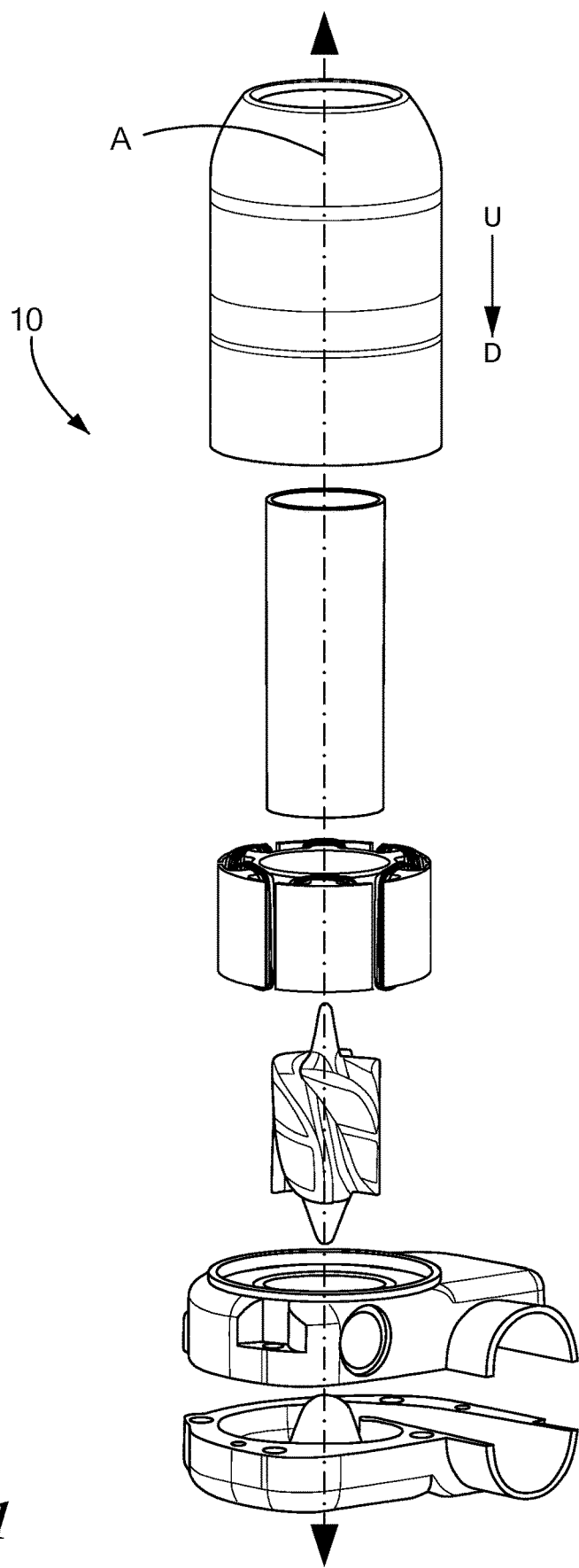
FIG. 1 is an exemplary implantable blood pump.

Before describing in detail exemplary embodiments, it is noted that the configurations reside primarily in combinations of system components and method steps related to responding to an adverse event associated with an implantable blood pump. Accordingly, the system and method components have been represented where appropriate by conventional symbols in the drawings, showing only those specific details that are pertinent to understanding the configurations of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Referring now to the drawings in which like reference designators refer to like elements there is shown in FIG. 1 an exemplary implantable blood pump 10 configured to be implanted within a patient, such as a human or animal patient. The blood pump 10 may be, without limitation, the HVAD® Pump or the MVAD® Pump, having a movable element, such as a rotor, configured to pump blood from the heart to the rest of the body. The HVAD® Pump is further discussed in U.S. Pat. Nos. 7,997,854 and 8,512,013, the disclosures of which are incorporated herein by reference in the entirety. The MVAD® Pump is further discussed in U.S. Pat. Nos. 8,007,254, 8,419,609, and 9,561,313, the disclosures of which are incorporated herein by reference in the entirety.

Figure 2:
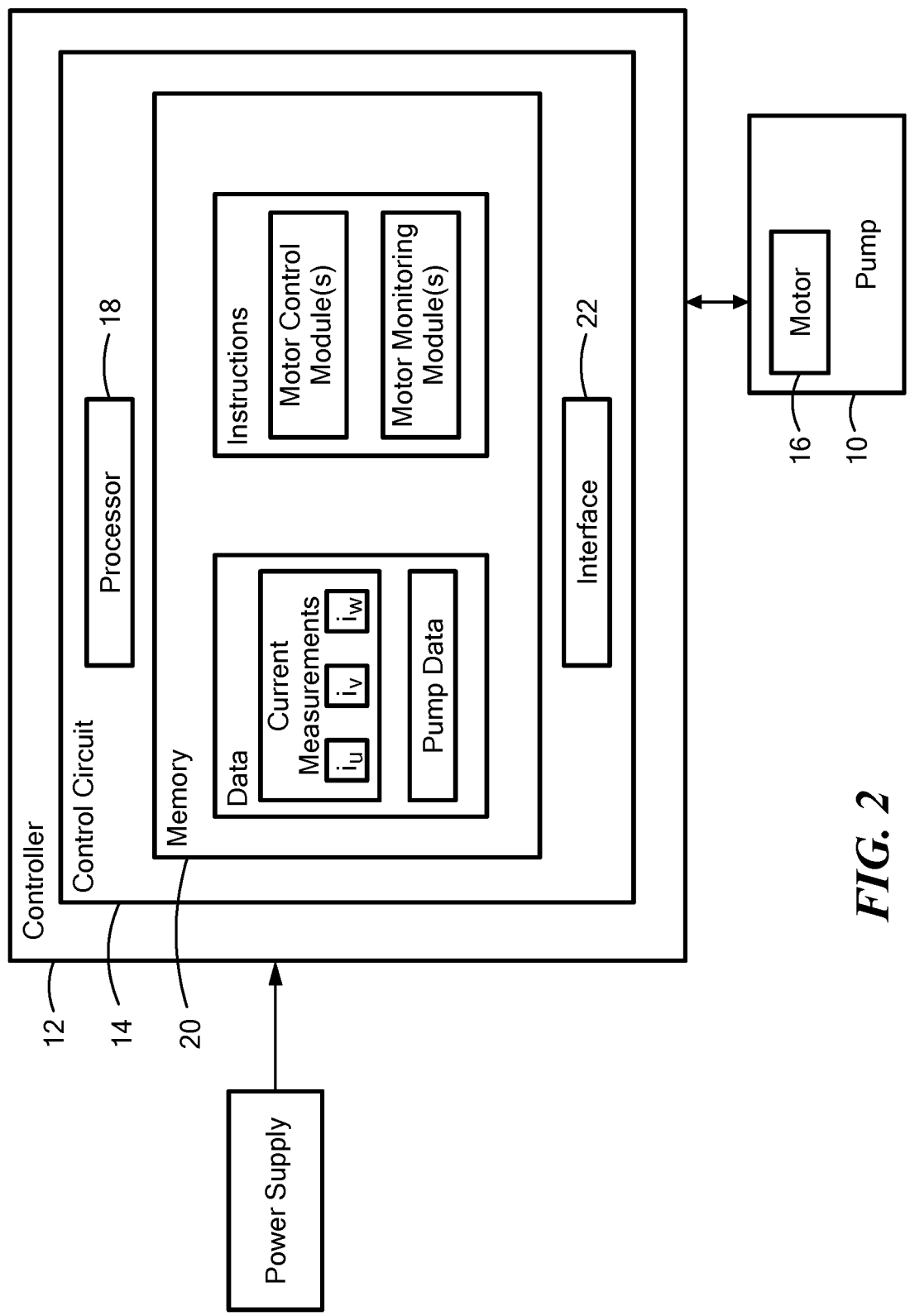
FIG. 2 is a block diagram of a system for responding to an adverse event associated with the implantable blood pump of FIG. 1.

With reference to FIG. 2, a block diagram is depicted of an exemplary system which includes the blood pump 10. In one configuration, the blood pump 10 may be in communication with a controller 12 and a control circuit 14 for monitoring and controlling startup and subsequent operation of a motor 16 implanted within the blood pump 10, as well as performing one or more of the method steps disclosed herein. The method and system disclosed herein may be used with axial or centrifugal blood pumps.

For example, the controller 12 may be configured to determine or detect a presence of an adverse event associated with the blood pump 10, such as a suction, occlusion or high-pressure event. In order to detect the adverse event, the controller may be configured to determine, monitor, and/or track one or more of the blood pump's parameters, for example, power usage amount, electrical current, voltage, and/or back electromotive force ("BEMF") as disclosed in commonly owned U.S. Pat. No. 9,511,179, which is incorporated by reference herein in the entirety. As commonly understood by a person of ordinary skill in the art, BEMF is the voltage in a coil of the motor that opposes current flowing through the coil, when the armature rotates. Following such detection, the controller 12 may execute an integrated response strategy including numerous speed reduction responses which may vary depending upon the type of adverse event detected.

The controller 12 may also include a processor 18 in communication with the control circuit 14, a memory 20, and an interface 22. The memory 20 may be configured to store information accessible by the processor 18, including instructions executable by the processor 18 and/or data that may be retrieved, manipulated or stored by the processor 18. Further details associated with an exemplary controller 12 are disclosed in commonly owned U.S. patent application Ser. No. 15/710,323, which is incorporated by reference herein in the entirety.

Figure 3:
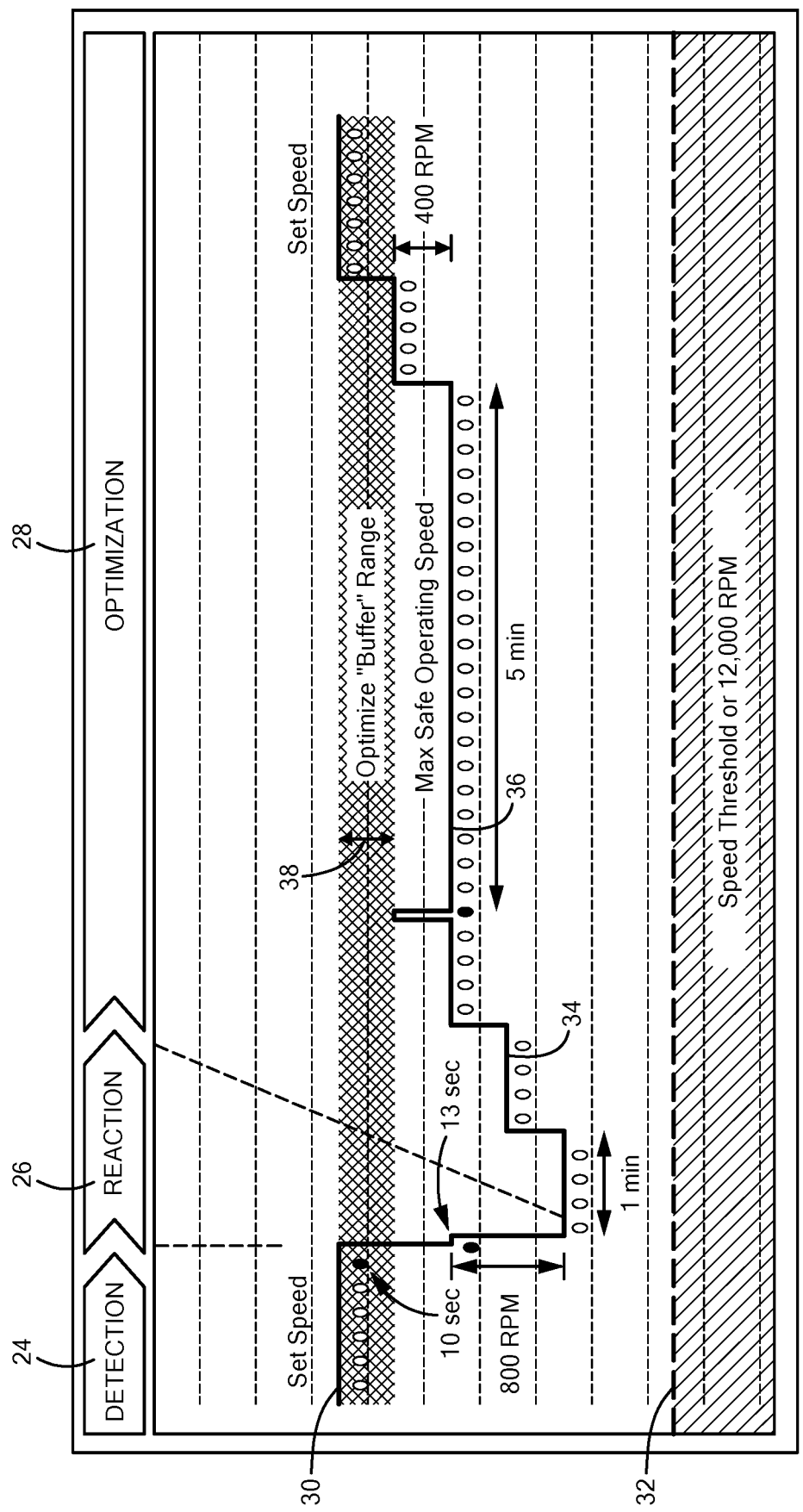
FIG. 3 is a response diagram in accordance with a method of responding to the adverse event associated with the implantable blood pump of FIG. 1.

Referring now to FIG. 3, an exemplary response diagram is provided including a detection phase 24, a reaction phase 26, and an optimization phase 28 of the method configured to imitate how a clinician would respond to an adverse event. In one configuration, the detection phase 24 includes detecting the adverse event, i.e., a first adverse event, which may be a suction event or a high-pressure event. The suction event includes a suction condition or occlusion condition, such as inflow occlusion. The high-pressure event includes a high-pressure condition, such as a relatively large pressure head build up across the blood pump 10 associated with low pump flow. In other words, the high-pressure condition may be a condition that includes a pressure within the blood pump 10 exceeding a pressure threshold determined in accordance with individual patients and pump parameters. Various adverse detection methods are described herein which may utilize pump parameter measurements and/or values to detect the adverse event.

In response to the detected adverse event, the reaction phase 26 includes the controller 12 being configured to execute a speed reduction response. Instructions associated with the response may be stored in the memory 20. During the speed reduction response, the method includes reducing a pump speed of the blood pump 10 relative to a set pump speed, generally designated in FIG. 3 as "30." The set pump speed 30 may be a preprogrammed pump speed programmed by a clinician or other healthcare provider, authorized to execute such programming.

The speed reduction response may differ in accordance with the type of adverse event, such as the suction or high-pressure event. For example, when the detected adverse event is a suction event, the pump speed may be reduced relative to the set pump speed 30 in one or more rapid step-wise decreases. Following each decrease, the method includes determining whether the adverse event has cleared and if so, the speed decrease ceases so as to minimally impact the patient and pump operations. In another example, when the detected adverse event is the high-pressure event, the pump speed may be reduced relative to the set pump speed 30 in a single speed decrease. The single speed decrease may cause a reduction in pump speed equal to an operating speed where the high-pressure condition cannot exist. In one exemplary configuration, the pump speed may be reduced by approximately 800 rotations per minute (RPM) over a 12 to 15 second duration as a result of a detected suction event. Although FIG. 3 depicts the speed decrease increments being 800 RPM, other speed increments may be utilized. In some instances, the reaction to the high-pressure condition may be more aggressive than that which occurs following the detected suction event as the high-pressure condition may indicate a higher risk factor for the patient and pump operations if not resolved relatively quickly.

The reaction phase 26 may last for a time period which may vary on a case by case basis. As a safeguard, a predetermined low speed threshold 32 may be stored by a user in the memory 20 and the controller 12 may be configured to prevent the pump speed from decreasing below the low speed threshold 32. In attempt to further increase the safety of the system, the controller 12 may generate a first alarm when the pump speed is within 100 to 200 RPMs of the low speed threshold 32 which indicates that there has been a failure to clear the adverse event. In one configuration, the first alarm is an audible alarm that alerts the patient. In addition to or in lieu of alerting the patient, the alarm may be a visual or vibratory alarm sent wirelessly from the controller 12 to a remote location, such as a physician's office.

After the reaction phase 26 and during the optimization phase 28, the method includes the controller 12 determining whether the initially detected adverse event or a second adverse event are present despite the reduction in pump speed. In other words, the controller 12 determines whether at least one adverse event is present. If neither the first or the second adverse event are present, the pump speed is increased to the set pump speed 30 in a gradual step-wise manner 34. If the first or the second adverse event, i.e., at least one adverse event, is detected while attempting to increase the pump speed to the set pump speed 30, the control circuit 14 performs an optimization attempt 36 in which the pump speed is reduced to a previous speed, such as a maximum safe operating speed ("MSOS") where no adverse events were previously detected. The MSOS may be maintained for a waiting period between 4 to 6 minutes or as otherwise predetermined. Once the waiting period is completed without the occurrence of an adverse event, a second attempt to return to the pump speed to the set pump speed 30 is performed in the gradual step-wise manner 34. Each attempt to return to the set pump speed 30 may identify a new MSOS based on the occurrence of adverse events.

Referring still to FIG. 3, the blood pump 10 may operate within an optimization range 38 that includes a range of speeds relatively close to the set pump speed 30 where the blood pump 10 is safe to operate without triggering a second alarm which indicates that there has been a failure to optimize after a predetermined number of attempts. For example, the optimization range 38 may be within 300 to 500 RPMs below the set pump speed 30 and may be stored in the memory 20. The optimization range 38 may be programmed by the clinician or as a fixed percentage of the set pump speed 30. The second alarm may be generated when the system has undergone at least three optimization attempts 36 but has been unsuccessful at returning to the set pump speed 30 without encountering an adverse event and the current pump speed is below the programmed optimization range 38. The second alarm may be audible, visual, vibratory, or the like, and may alert the patient and/or may be sent wirelessly from the controller 12 to a remote location, such as the physician's office.

Figure 4:
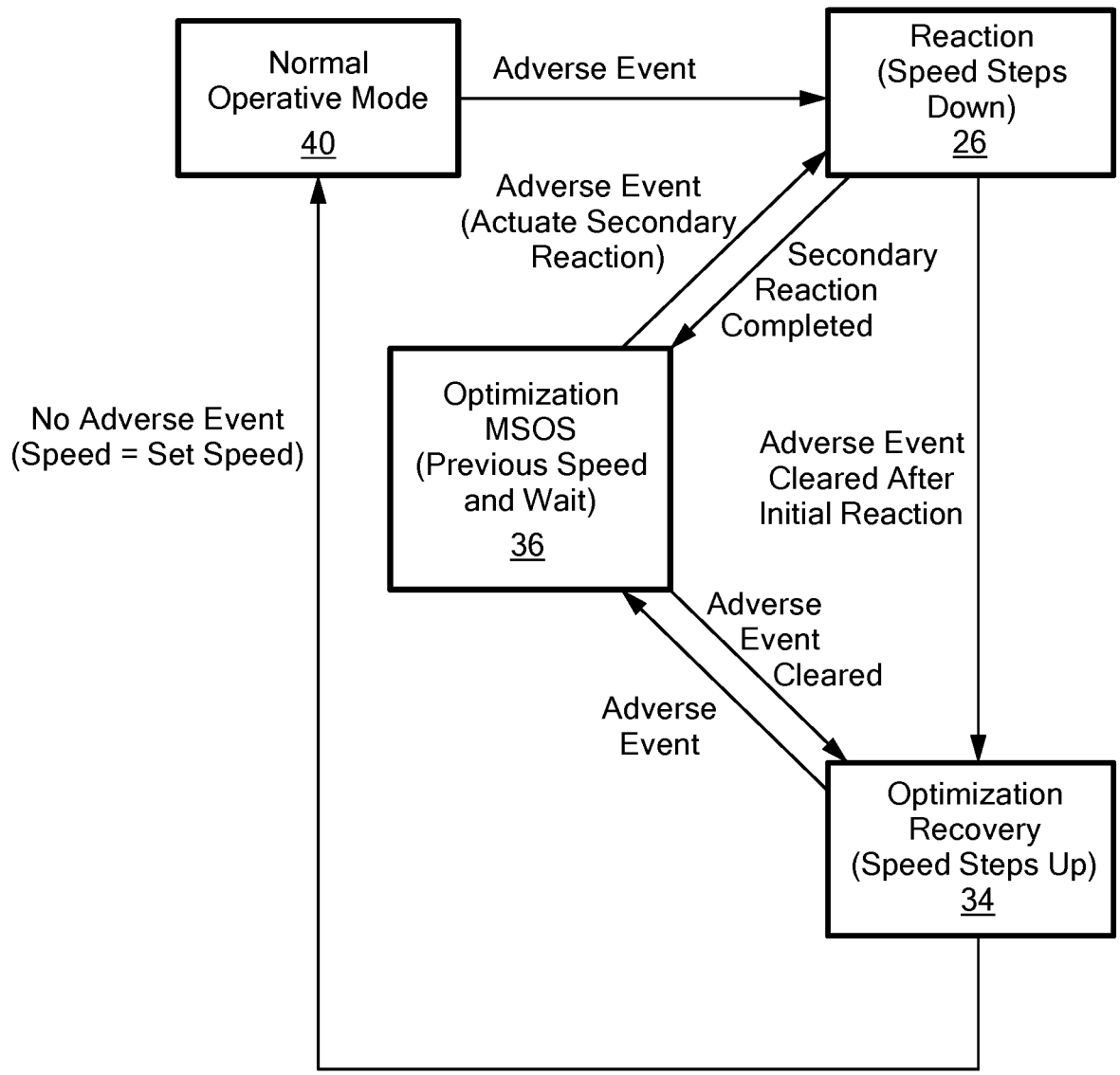
FIG. 4 is a diagram of an integrated response strategy and transition associated with the method of FIG. 3.

With reference to FIGS. 3 and 4, after the optimization attempt 36 at the MSOS, the controller 12 is configured to determine whether the first or the second adverse event are present and if not, the speed is gradually increased back to the set pump speed 30 in a normal operative mode 40. In other words, if the first and second adverse events are cleared, the speed is gradually increased to the normal operative mode. The gradual speed increase is configured to provide the patient's heart time to adapt to the changing loading conditions and reduce or prevent the occurrence of a second adverse event. Although FIG. 3 depicts the speed increase being 400 RPM, other speed increments may be utilized.

With reference to FIG. 4, if the controller 12 determines that the first or the second adverse event are present after the optimization attempt 36, the pump speed may return to the reaction phase 26 where the pump speed is reduced during a secondary reaction in an attempt to clear the adverse condition. The process associated with the secondary reaction varies depending upon whether the adverse condition is the suction or high-pressure event.

After the secondary reaction, the pump speed may be increased and maintained during a second optimization attempt 36. If the adverse event has cleared after the second optimization attempt 36, the method includes the controller 12 returning the blood pump 10 to the set pump speed 30 in the normal operative mode 40. If the adverse event occurs during the second optimization attempt 36, the reaction phase 26 and the optimization attempt 36 may be repeated. The blood pump 10 may operate within the optimization phase 28 indefinitely if the adverse condition persists. A clinician may be alerted that the optimization attempt 36 is in progress by way of the second alarm, a signal sent to the clinician's monitor, or the like, to explain why the pump speed is not equal to the set pump speed 30.

Figure 5:
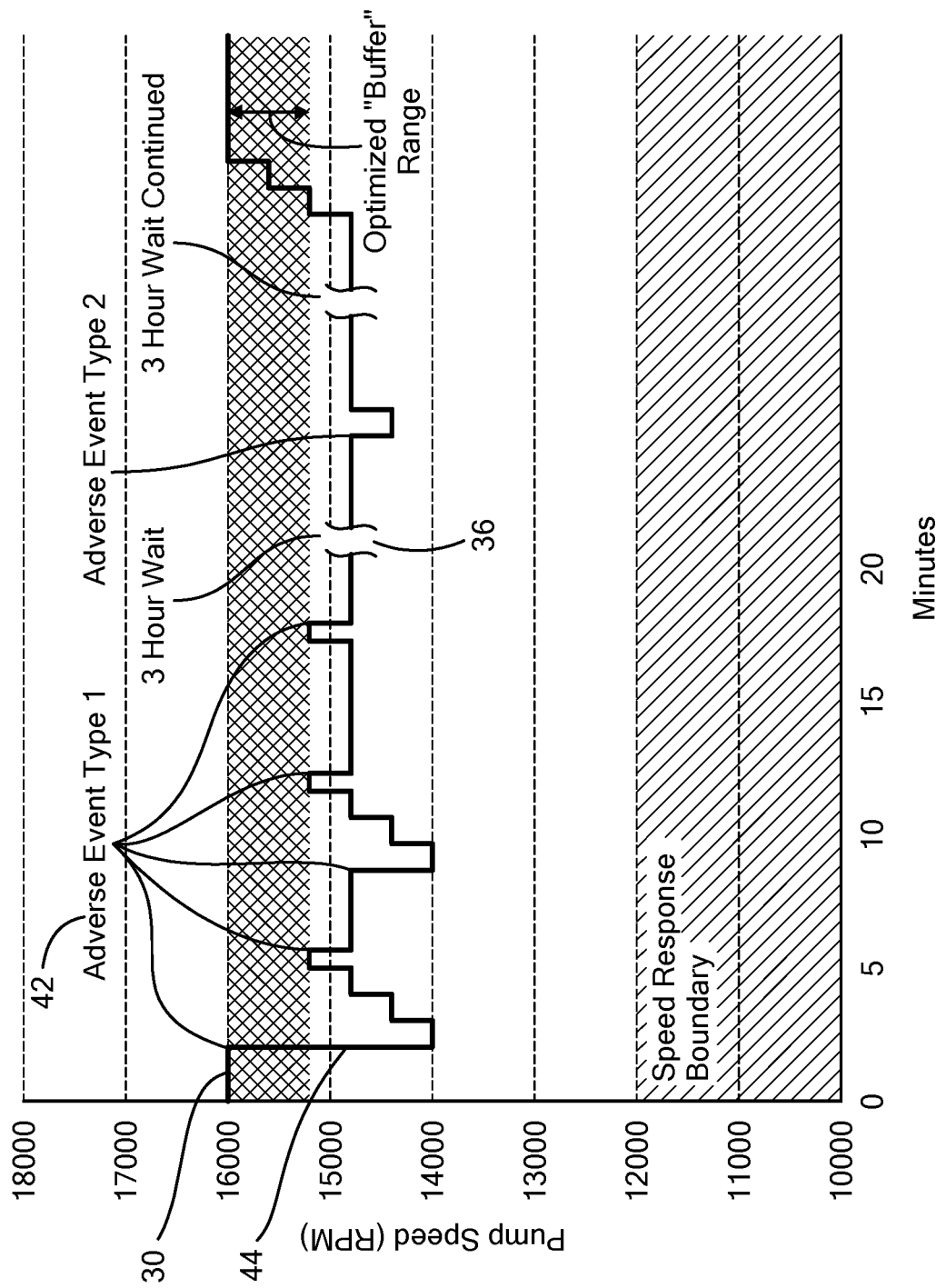
FIG. 5 is a graph depicting a primary reaction followed by a secondary reaction in accordance with the method of FIG. 3.

With reference to FIG. 5, in one configuration, the method includes the controller 12 continuously monitoring the blood pump 10 to detect the presence of one or more adverse events, which are responded to by the integrated response strategy. In particular, such detection includes the controller 12 utilizing at least two detection algorithms or inputs to continuously monitor the blood pump 10 at numerous speeds, such as between 12 to 18 kRPM. For example, FIG. 5 depicts a detected first adverse event 42 which may be a high-pressure conditioned, followed by a primary reaction 44 including a single speed decrease performed in an attempt to clear the high-pressure condition. Following the primary reaction 44, the pump speed may enter the optimization phase 28. If the first adverse event 42 or another adverse event are detected the pump speed may return to the MSOS. One or more secondary reactions including one or more rapid step-wise decreases may be performed throughout a secondary reaction phase as part of the reaction phase 26 or the optimization phase 28 in response to a detected suction event. In other words, the primary and secondary reactions may be performed singularly or in combination following the detected adverse events to provide a system that is relatively simple to operate and which responds to the adverse events using a cohesive strategy.

In another example, if the controller 12 simultaneously detects the first adverse event as a high-pressure condition and a second adverse event as a suction condition, the method includes reducing the pump speed relative to the set pump speed 30 using either the rapid step-wise decrease or the single speed decrease, whichever is a lower reaction response. The method and system disclosed herein are not confined to a particular number of detection algorithms or inputs, one or more of which may detect pre-event conditions prior to an onset of the adverse event as preventative measures. For example, the method and system may include detecting warning signs of a pre-suction condition and attempting to resolve the condition before the condition increases in severity.

With reference to FIGS. 6-9, one or more suction detection methods may be used to detect the suction or occlusion condition, such as when the pump speed is between 12 to 18 kRPMs as referenced above. In one exemplary configuration, the suction methods include an input signal being a 50 Hz-100 Hz Back Electro Motive Force ("BEMF") waveform; however, other measurement units may be used. Further examples and explanations of suction detection methods and pump pressure algorithms are provided in commonly owned U.S. Pat. Nos. 9,492,601, 9,427,508, and U.S. Patent Pub. No. 2015/0367048, all of which are incorporated herein in the entirety.

Figure 6:
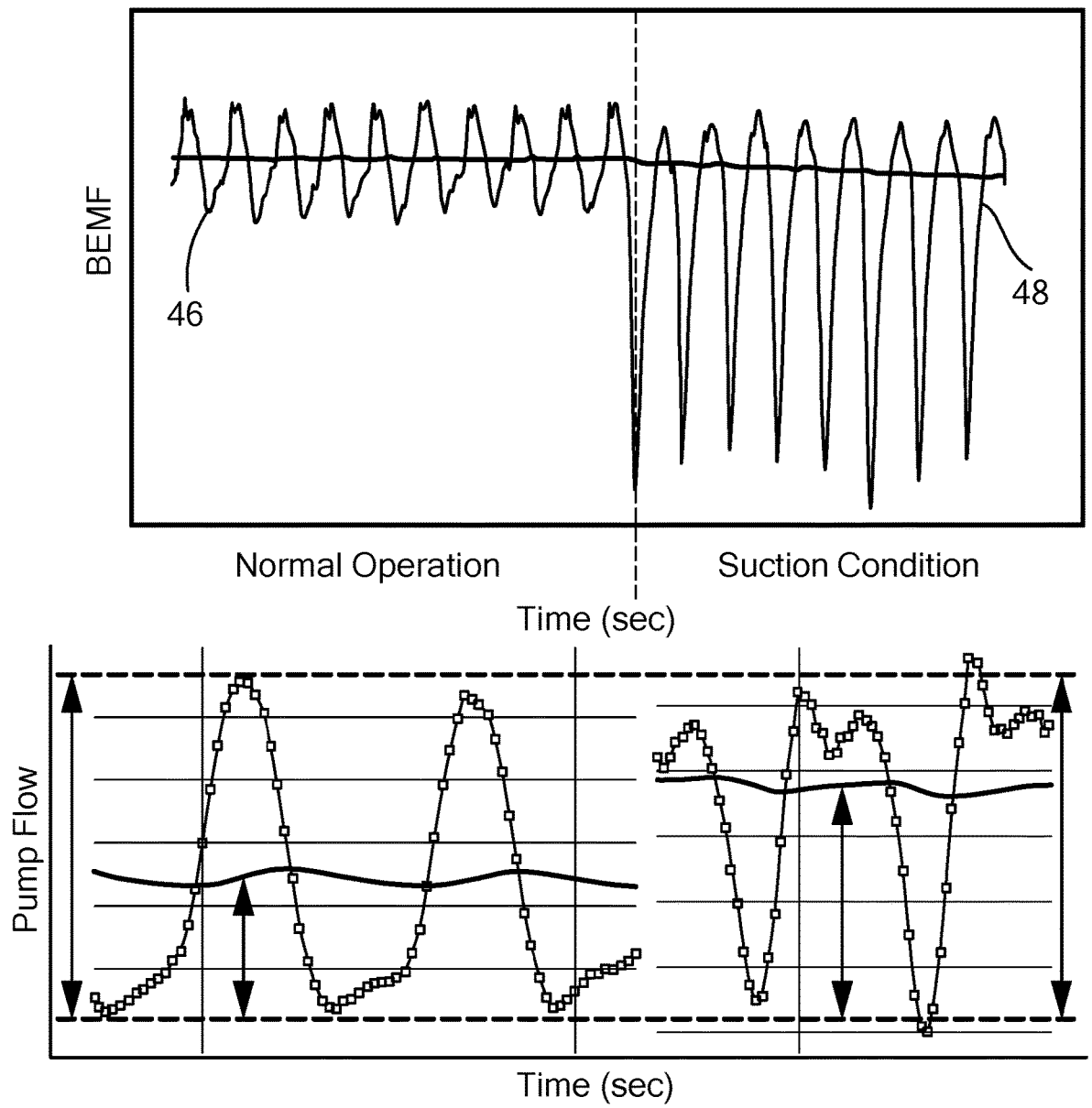
FIG. 6 is an exemplary graph depicting a pump flow waveform under a normal operation and a suction condition.
Figure 7:
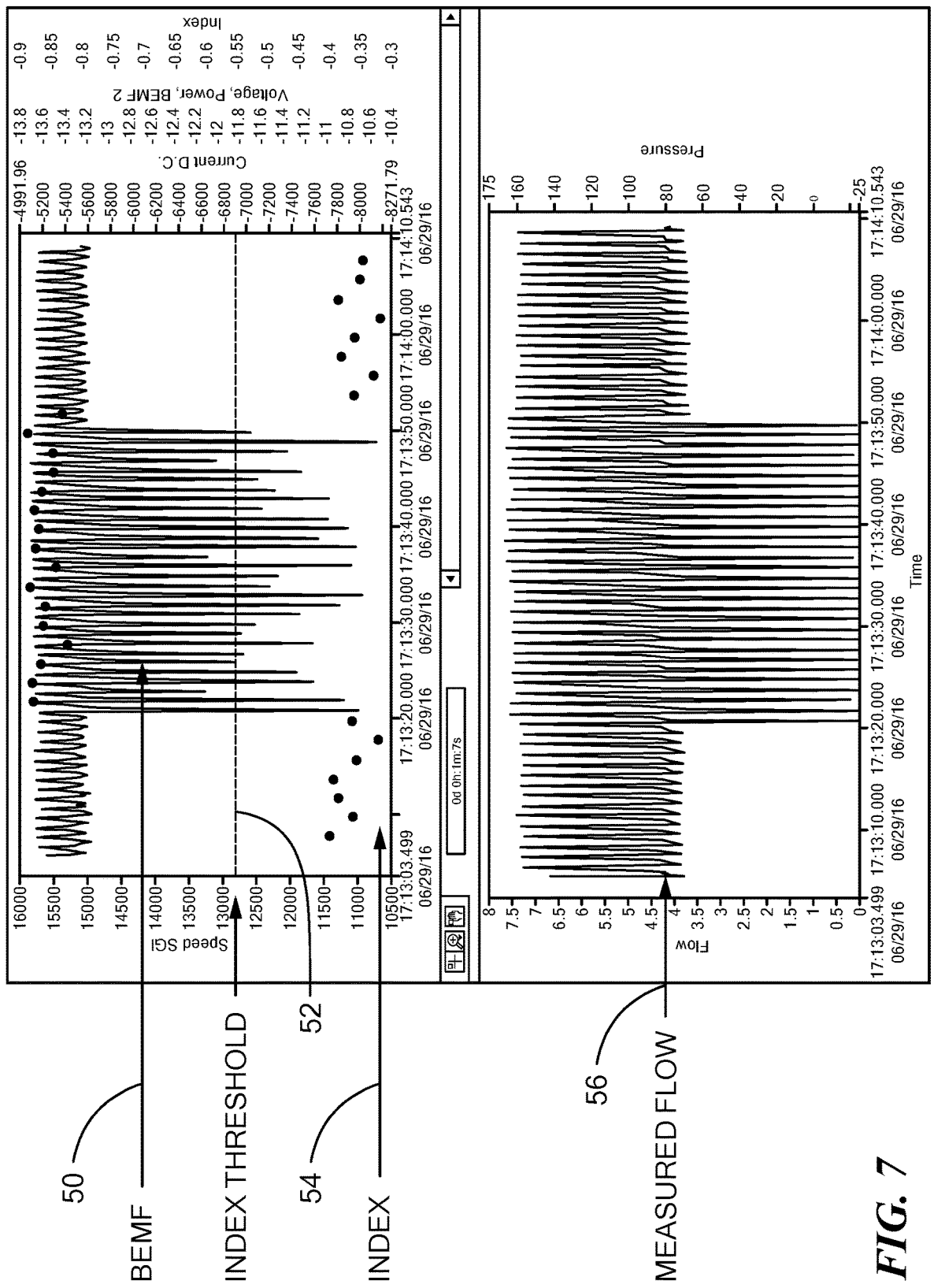
FIG. 7 is an exemplary graph depicting a suction condition.

In one configuration, a first suction detection method uses a ratio of a running average, a maximum, and a minimum of a BEMF signal to detect the suction condition. In particular, the suction detection method may utilize an equation (AVG−MIN)/(MAX−MIN) to calculate an index during a time interval, such as every 2 seconds. With reference to FIG. 6, a BEMF waveform and a pump flow waveform are shown plotted over time (seconds) during normal operation 46 and during the suction condition 48. With reference to FIG. 7, a presence of the suction condition is indicated when the ratio of the running average, the maximum, and the minimum of the BEMF signal 50 exceeds a predetermined threshold 52, such as 0.65. In other words, an index value greater than 0.65 may be a common indication of the suction event. In other configurations, the threshold may be an adaptive threshold. FIG. 7 also depicts an adverse event index 54 and a measured pump flow 56 during the suction event. The predetermined threshold 52 and index value greater than 0.65 are provided for exemplary purposes only and may vary in accordance with preclinical and clinical data, such as that which is obtained following an analysis of in vitro testing over a range of fluid viscosities, heart rates, speeds, pulsatility levels, and average flows.

Figure 8:
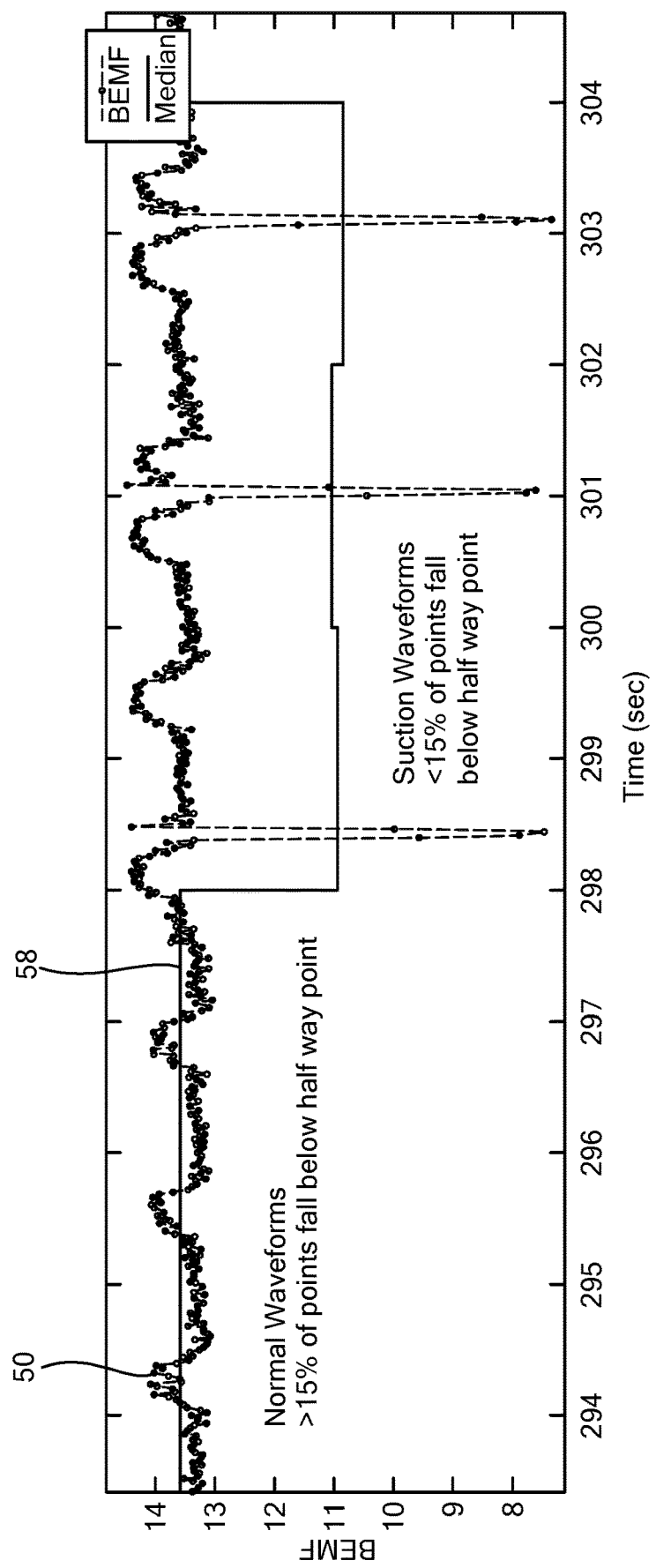
FIG. 8 is an exemplary graph depicting another configuration of a suction detection method.

With reference to FIG. 8, in another configuration, a second suction detection method includes calculating an index using a percentage of plotted points that fall below a mid-point (MAX−MIN/2) or median 58 of the BEMF signal 50. The index may be calculated during a time interval, such as every 2 seconds. In one configuration, one or more normal waveforms may be indicated by a percentage, such as 15% or more of the waveform's plotted points, falling below the median 58. In such a configuration, a relatively low ratio of plotted points, such as less than 15% of the plotted points, falling below the median 58 may indicate one or more suction conditions. Other percentages or thresholds may be used and determined through analysis of preclinical data with further revisions occurring through clinical data.

Figure 9:
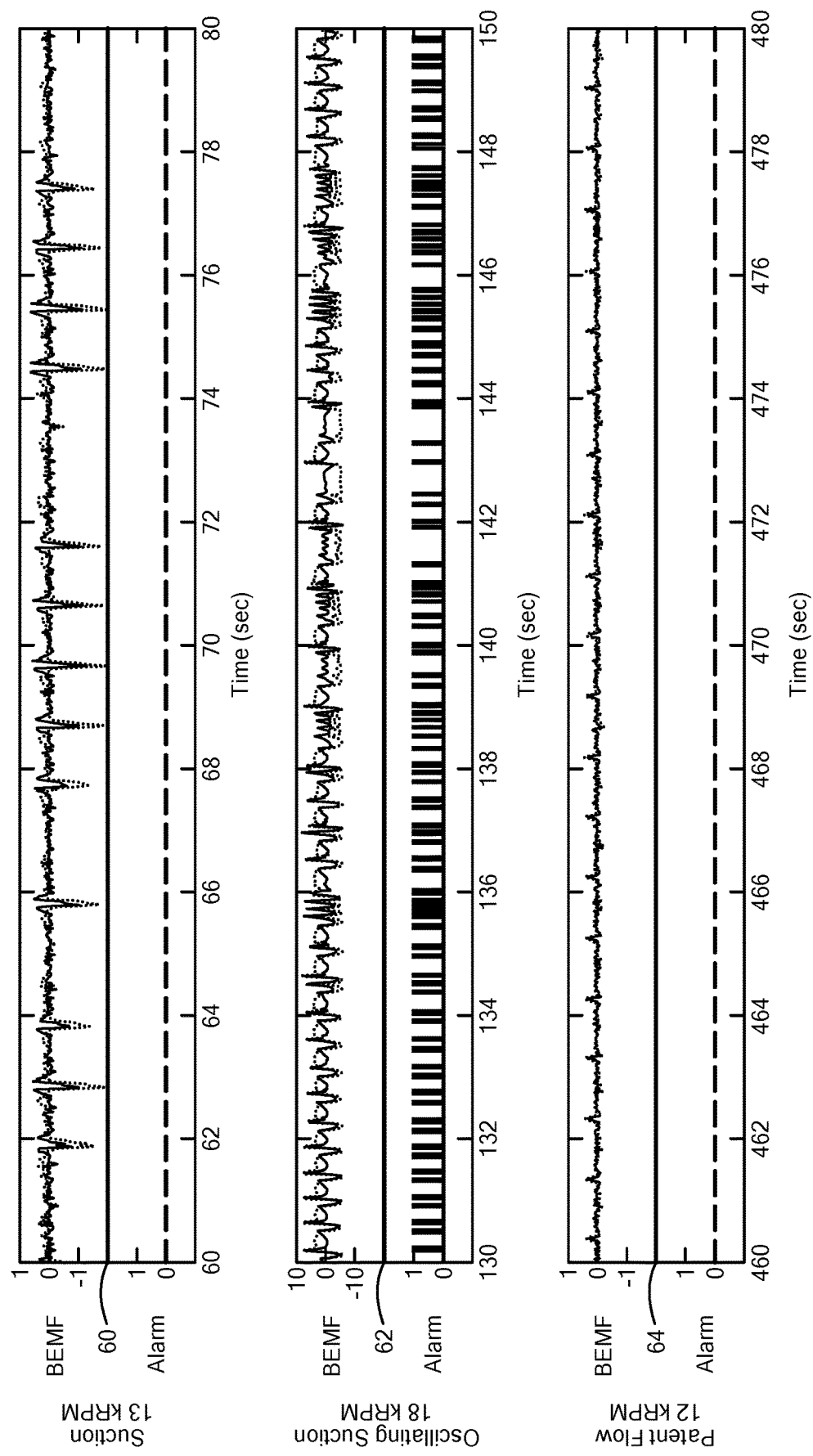
FIG. 9 is a plurality of exemplary graphs depicting a pump flow signal and a set of three time windows illustrating the behavior of a Back Electro Motive Force ("BEMF") signal or alarm signal under an oscillating suction, a suction, and a patent flow condition.

In another configuration, a third suction detection method includes applying frequency-based methods, such as filtering to the BEMF signal 50. More specifically, a digital filter with a designated cutoff frequency may be applied to the BEMF signal 50 to detect a flow pattern, such as an oscillating suction flow pattern. With reference to FIG. 9, a pump flow signal and a set of three-time windows are depicted illustrating the behavior of a BEMF signal or alarm signal under oscillating suction, suction, and patent flow conditions. The suction flow pattern at 13kRPM is generally designated at "60," the oscillating suction flow pattern at 18 kRPM is generally designated as "62," and the patent flow condition at 12 kRPM is generally designated as "64." The cutoff frequency may vary and may be determined through analysis of preclinical data, with further revisions occurring with clinical data.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of responding to adverse events associated with an implantable blood pump, the method comprising:
   monitoring, by circuitry in communication with the implantable blood pump, one or more pump parameters of the implantable blood pump;
   detecting, based on the one or more pump parameters, a first adverse event, the first adverse event being a suction event;
   reducing a pump speed relative to a pump set speed in a plurality of consecutive and rapid step-wise decreases in response to the first adverse event being detected;
   determining whether the first adverse event is present following each of the plurality of consecutive and rapid step-wise decreases of the reduction of the pump speed;
   determining whether a second adverse event different than the first adverse event is present, based on the one or more pump parameters, following the reduction of the pump speed;
   in response to the first adverse event not being present and the second adverse event not being present, increasing the pump speed to the set pump speed; and
   in response to the first adverse event or the second adverse event being present while increasing the pump speed to the set pump speed, performing a single speed decrease to reduce the pump speed to a maximum safe operating speed, wherein the single speed decrease causes a greater reduction in the pump speed than each of the plurality of consecutive and rapid step-wise decreases, and wherein the maximum safe operating speed comprises a speed at which the first adverse event and the second adverse event have not been previously detected to occur in the implantable blood pump.

2. The method of claim 1, further comprising:
   detecting a clearance of the first adverse event; and
   gradually increasing the pump speed to the set pump speed in response to detecting the clearance.

3. The method of claim 1, further comprising maintaining the maximum safe operating speed during an optimization attempt.

4. The method of claim 3, further comprising:
   in response to detecting at least one of the first adverse event or the second adverse event following the optimization attempt, reducing the pump speed to the maximum safe operating speed.

5. The method of claim 3, further comprising:
   in response to detecting the first adverse event or the second adverse event during the optimization attempt, reducing the pump speed to the maximum safe operating speed.

6. The method of claim 1, further comprising:
   determining whether a clearance of the first adverse event has occurred following each of the plurality of consecutive and rapid step-wise decreases; and discontinuing the plurality of consecutive and rapid step-wise decreases in response to the clearance of the first adverse event being detected.

7. The method of claim 1, further comprising generating a first alarm in response to the pump speed reaching a predetermined low speed threshold and the first adverse event not being cleared.

8. The method of claim 1, further comprising generating a second alarm in response to the pump speed being below a predetermined optimization range after a predefined number of attempts to optimize to the set pump speed.

9. The method of claim 1, further comprising detecting the first adverse event based on a difference between an average and a minimum of a back electromotive force signal multiplied by a difference between a maximum and the minimum of the back electromotive force signal.

10. The method of claim 1, further comprising:
monitoring the implantable blood pump for occurrences of the adverse events to determine the maximum safe operating speed.

11. A system for responding to adverse events associated with an implantable blood pump, the system comprising:
a processor and a control circuit in communication with the processor and the implantable blood pump, the control circuit being configured to:
monitor one or more pump parameters of the implantable blood pump;
detect, based on the one or more pump parameters, a first the adverse event, the first adverse event being suction;
execute a speed reduction response including reducing a pump speed of the implantable blood pump relative to a set pump speed in a plurality of consecutive and rapid step-wise decreases in response to the first adverse event;
determine whether the first adverse event is present following each of the plurality of consecutive and rapid step-wise decreases of the speed reduction response;
determine whether a second adverse event different than the first adverse event is present, based on the one or more pump parameters, following the speed reduction response;
in response to the first adverse event not being present and the second adverse event not being present, increase the pump speed to the set pump speed; and
in response to the first adverse event or the second adverse event being present while increasing the pump speed to the set pump speed, performing a single speed decrease to reduce the pump speed to a maximum safe operating speed, wherein the single speed decrease causes a greater reduction in the pump speed than each of the plurality of consecutive and rapid step-wise decreases, and wherein the maximum safe operating speed comprises a speed at which the first adverse event and the second adverse event have not been previously detected to occur in the implantable blood pump.

12. The system of claim 11, wherein the control circuit is further configured to:
detect a clearance of the first adverse event; and
cause the pump speed to gradually increase to the set pump speed in response to detecting the clearance.

13. The system of claim 11, wherein the control circuit is further configured to maintain the maximum safe operating speed during an optimization attempt.

14. The system of claim 13, wherein the control circuit is further configured to, in response to detecting at least one of the first adverse event or the second adverse event following the optimization attempt, cause the pump speed to reduce to the maximum safe operating speed.

15. The system of claim 13, wherein the control circuit is further configured to, in response to detecting the first adverse event or the second adverse event during the optimization attempt, cause the pump speed to reduce to the maximum safe operating speed.

16. The system of claim 11, wherein the control circuit is further configured to:
determine a clearance of the first adverse event following each of the plurality of consecutive and rapid step-wise decreases; and
discontinue the plurality of consecutive and rapid step-wise decreases in response to the clearance of the first adverse event being detected.

17. The system of claim 11, wherein the control circuit is further configured to generate a first alarm in response to the pump speed reaching a predetermined low speed threshold and the first adverse event not being cleared.

18. The system of claim 11, wherein the control circuit is further configured to generate a second alarm in response to the pump speed being below a predetermined optimization range after a predefined number of attempts to optimize to the set pump speed.

19. The system of claim 11, wherein the control circuit is further configured to detect the first adverse event based on a difference between an average and a minimum of a back electromotive force signal multiplied by a difference between a maximum and the minimum of the back electromotive force signal.

20. The system of claim 11, wherein the control circuit is further configured to monitor the implantable blood pump for occurrences of the adverse events to determine the maximum safe operating speed.

* * * * *